(12) United States Patent
Sada et al.

(10) Patent No.: US 8,536,350 B2
(45) Date of Patent: Sep. 17, 2013

(54) PROCESS FOR THE MANUFACTURE OF DRONEDARONE

(75) Inventors: Mara Sada, Segrate (IT); Antonio Nardi, Segrate (IT); Stefano Maiorana, Milan (IT)

(73) Assignee: Laboratorio Chimico Internazionale S.p.A., Milan (IT)

( * ) Notice: Subject to any disclaimer, the term of this patent is extended or adjusted under 35 U.S.C. 154(b) by 0 days.

(21) Appl. No.: 13/580,005

(22) PCT Filed: Jan. 26, 2011

(86) PCT No.: PCT/IB2011/000113
§ 371 (c)(1),
(2), (4) Date: Sep. 7, 2012

(87) PCT Pub. No.: WO2011/104591
PCT Pub. Date: Sep. 1, 2011

(65) Prior Publication Data
US 2012/0330037 A1 Dec. 27, 2012

(30) Foreign Application Priority Data
Feb. 23, 2010 (IT) ............................ MI2010A0284

(51) Int. Cl.
*A61K 31/34* (2006.01)
*C07D 307/00* (2006.01)

(52) U.S. Cl.
USPC ............................ 549/468; 549/467; 514/469

(58) Field of Classification Search
CPC .............................. C07D 307/00; A61K 31/34
See application file for complete search history.

(56) References Cited

FOREIGN PATENT DOCUMENTS

| WO | WO 2009/044143 | | 4/2009 |
|---|---|---|---|
| WO | WO 2009/044143 A2 | * | 4/2009 |

OTHER PUBLICATIONS

PCT Notification Concerning Transmittal of International Preliminary Report on Patentability (Chapter 1 of the Patent Cooperation Treaty), mailed Sep. 7, 2012; International Application No. PCT/IB2011/000113, Filed Jan. 26, 2011 (1 pg).
PCT International Preliminary Report on Patentability; International Application No. PCT/IB2011/000113, International filing date Jan. 26, 2011 (5 pgs).
International Search Report for PCT/IB2011/000113 mailed Apr. 11, 2011.
Written Opinion of the International Searching Authority mailed Apr. 11, 2011.
Search Report for IT MI 2010A000284 dated Sep. 27, 2010.
Lis et al., "Synthesis and Antiarrythmic Activity of Novel 3-alkyl-1-[omega-[4-] (alkylsulsony) amino] phenyl]-omega-hydroxyalkyl]-1H-imidazolium salts and related compounds", Journal of Medicinal Compounds, vol. 30, 1987. pp. 696-704.

* cited by examiner

*Primary Examiner* — Rita Desai
*Assistant Examiner* — Ben S Michelson
(74) *Attorney, Agent, or Firm* — Nixon & Vanderhye P.C.

(57) ABSTRACT

The invention relates to a new process for the preparation of dronedarone and its salts, in particular a synthesis process which allows said compound and its salts to be obtained with good yields, high purity and in an industrially expedient manner; the invention also concerns a new synthesis intermediate.

10 Claims, No Drawings

PROCESS FOR THE MANUFACTURE OF DRONEDARONE

This application is the U.S. national phase of International Application No. PCT/IB2011/000113 filed 26 Jan. 2011 which designated the U.S. and claims priority to IT MI2010A000284 filed 23 Feb. 2010, the entire contents of each of which are hereby incorporated by reference.

SUMMARY

The present invention relates to a new process for the preparation of dronedarone and its salts, in particular a synthesis process which allows said compounds to be obtained with good yields, high purity and in an industrially expedient manner. The invention also concerns a new synthesis intermediate.

TECHNICAL BACKGROUND

The compound with chemical name N-[2-butyl-3-(4-(3-(dibutylamino) propoxy)benzoyl)-5-benzofuranyl]methanesulfonamide, the international non-proprietary name of which is "dronedarone", has the following formula (I)

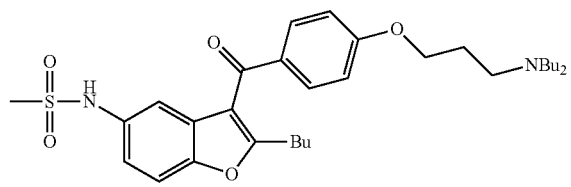

(I)

in which "Bu" represents n-butyl.

Dronedarone is a drug that has been marketed for some time for the treatment of cardiac arrhythmias.

The known syntheses of dronedarone are very complex and entail introduction of the different functional groups on the benzofuran ring via several steps and purifications, to the detriment of the yields and industrial applicability of said processes.

WO2009/044143 describes a process for the synthesis of dronedarone, which entails reacting 2-butyl-3-(4-hydroxybenzoyl)-5-nitrobenzofuran with a derivative of protected dibutylamine, reducing the nitro group, mesylating and lastly converting the derivative obtained into a salt thereof

DISCLOSURE OF THE INVENTION

An object of the present invention is to provide a process for the preparation of dronedarone which is simple to implement industrially, which provides good yields and which comprises easily purifiable intermediate compounds.

Thus according to one of its aspects, the invention concerns a process for the preparation of the dronedarone of formula (I), above, or a salt thereof, which comprises the following steps:

(a) reducing the nitro group of the compound of formula (II)

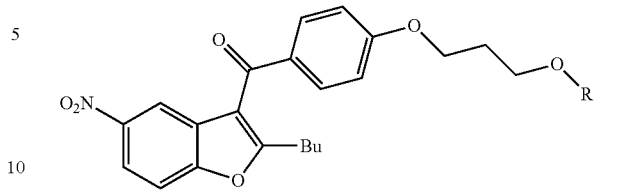

(II)

in which "Bu" represents n-butyl and R represents a hydrogen or a protecting group which is cleavable by hydrogenation, to yield the compound of formula (III)

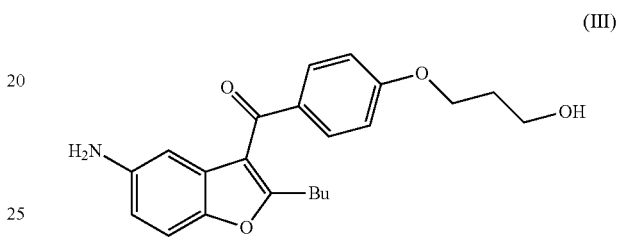

(III)

(b) bis-mesylating the compound (III) thus obtained to yield the compound of formula (IV)

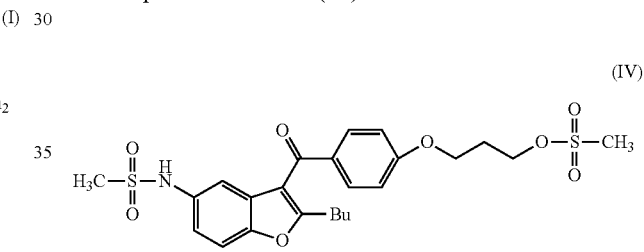

(IV)

(c) replacing the mesyloxy group of the compound (IV) with a dibutylamino group to obtain the dronedarone of formula (I)

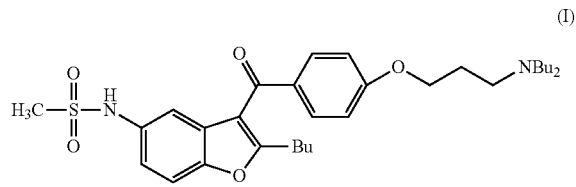

(I)

(d) optionally converting dronedarone into a salt thereof

According to an advantageous embodiment of the invention, the salts of dronedarone are pharmaceutically acceptable salts. A particularly preferred salt is hydrochloride. By "protecting group which is cleavable by hydrogenation" we mean, according to the present invention, a protecting group of the hydroxyl which is cleavable by catalytic hydrogenation; said groups are well known to a person skilled in the art and include, for example, the benzyl group or an allyl group.

Step (a)

The reduction step (a) of the nitro group can be performed with any reducing agent suitable for conversion of the nitro group into an amine group. According to a preferred embodiment of the invention, the reduction (a) is performed catalytically, using hydrogen for example in the presence of a catalyst of Pd/C or PtO$_2$ in an appropriate solvent, for example a lower alcohol, such as methanol, ethanol, 1-propanol, 2-propanol, butanol or mixtures thereof.

The reduction reaction can be conducted at a temperature between the room temperature and approximately 50° C., for example around 25-45° C., advantageously around 30° C.

The hydrogen can be supplied to the reaction under pressure, for example at a pressure of approximately 4 bars, in a suitable autoclave.

The development of the reaction can be followed according to the techniques known to a person skilled in the art, at the end of the reduction the catalyst may be removed by filtering and the desired compound can be isolated by concentration of the solvent and if necessary purified, for example by crystallisation.

Step (b)

The bis-mesylation step (b) allows the amine group formed in step (a) and the hydroxyl group present on the lateral chain to be simultaneously mesylated.

This step is particularly advantageous as it allows, by one single reaction, the introduction of the functional sulfonamide group (present on the final compound) and the replacement of the hydroxy group with the mesyloxy group, i.e. with an optimal leaving group, therefore suitable for subsequent replacement with the dibutylamino group.

The reaction can be performed with a mesylating agent, for example a mesyl halide, preferably mesyl chloride, in an appropriate solvent, for example a chlorinated solvent such as dichloromethane or acetonitrile, advantageously at temperatures below or equal to the room temperature. In particular, the first part of the reaction, relative to the addition of the mesylating agent, is preferably carried out at temperatures around 0° C., for example around 0-5° C., or even below, while continuation of the reaction is advantageously performed at room temperature. Naturally the mesylating agent will be used in sufficient quantities to mesylate the two functional groups (amine and hydroxy), therefore in molar quantities at least double with respect to the compound of formula (III), preferably more than double the moles of the compound of formula (III).

At the end of the mesylation reaction the desired compound is isolated according to the techniques well known to a person skilled in the art and, if necessary or desired, purified.

Step (c)

The step (c) for preparation of the dronedarone comprises replacement of the mesyloxy group with the dibutylamino group and is performed preferably in a suitable polar aprotic solvent such as dimethylformamide, acetonitrile, preferably acetonitrile, in the presence of dibutyl amine.

The reaction can be performed at temperatures just above room temperature and the final compound of formula (I), if desired or necessary, can be isolated according to the techniques known to a person skilled in the art.

Alternatively, dronedarone is not isolated and purified but is used a crude product in the salification step (d).

Step (d)

The salification step (d) is optional and, if desired, it is performed according to any method known to a person skilled in the art which allows preparation of the desired dronedarone salt, without altering the functional groups present on the molecule.

Thus for example the dronedarone can be converted into the hydrochloride salt, for salification with a hydrochloric acid in an appropriate solvent, as is well known to a person skilled in the art.

Technical details relative to the process of the invention will be provided in the following Experimental Section.

The compound of formula (IV) is a new molecule and constitutes a further subject of the invention, together with its salts and/or solvates.

The starting compound of formula (II) can be prepared according to any possible synthesis.

According to a preferred embodiment of the invention, the compound of formula (II) is prepared starting from a compound of formula (V)

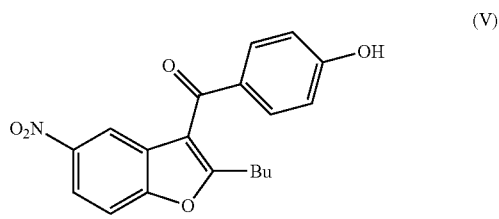

by reaction with a 3-halo-1-propanol for example 3-chloro-1-propanol, or a protected 3-halo-1-propanol, in appropriate reaction conditions. An example of this preparation is provided in the experimental section of the present description.

By "protected 3-halo-1-propanol" we mean here a 3-halo-1-propanol in which the hydroxyl group is protected with an R group as defined above.

According to another of its aspects, the invention also concerns preparation of the dronedarone according to the steps from (a) to (d) described above, in which the starting compound of formula (II) is synthesised starting from the compound of formula (V) indicated above, advantageously according to the synthesis process defined above.

All the intermediates of the reactions discussed above can be easily isolated and, if desired or necessary, purified by crystallisation. As is known, crystallisation is a simple method which is easy to carry out on an industrial scale (contrary to purifications by chromatography, for example).

In particular, the mesylation reaction is in general a critical reaction in the production of dronedarone and the product obtained normally requires accurate purification, almost always by chromatography. It has been observed, however, that when the mesylation reaction is not performed as the last reaction (i.e. when operating according to the present invention) it is possible to avoid purifying the mesylated intermediate by chromatography and nevertheless obtain a finished product with high yields and good purity. As said, simplicity of the purification methods is essential for satisfactory industrial production. Thus, operating as described in the present description, the dronedarone can be salified directly as it is not necessary to isolate and purify it at the end of step (c).

With respect to the processes of the prior art, the process of the invention allows dronedarone or its salts to be obtained in a pure manner and with good yields, without having to subject the reaction intermediates to further and laborious purification steps, also when the process is implemented on an industrial scale.

Repeating the processes of the prior art, the applicant has ascertained that said purification steps were necessary in order to obtain the dronedarone with the necessary pharmaceutical grade purity, with consequent negative repercussions on the overall yields of the process and on the costs of industrial production.

EXPERIMENTAL SECTION

Example 1

Step a

Preparation of the 3-{4-[(5-amino-2-butyl-1-benzofuran-3-yl)carbonyl]phenoxy}propan-1-ol ((Formula III))

180 g (0.453 mol) of 3-{4-[(2-butyl-5-nitro-1-benzofuran-3-yl) carbonyl]phenoxy}propan-1-ol (formula(II)) dissolved in 1800 ml of methanol are loaded in a glass Buchi autoclave. Subsequently 9 g of Pd/C 10% (50% $H_2O$) are added and $H_2$ is loaded at a pressure of 4 bars. The mixture is left under stirring maintaining the temperature below 40° C. Once the consumption of hydrogen is complete, the reaction is left under stirring for approximately one further hour until it reaches 25° C. The catalyst is filtered on a Celite panel and the alcoholic solution containing the product is concentrated to residue. The crude product is crystallised, recovering it with 400 ml of toluene and the product is dried under a vacuum at 40° C. for 6-7 hours. 151 g of the product in the title are obtained.

Yield: 91%

$^1$HNMR ($CDCl_3$, 300 MHz): δ=0.87 (3H, t); 1.35 (2H, m); 1.72 (2H, m); 2.08 (2H, m); 2.84 (2H, t); 3.88 (2H, t); 4.20 (2H, t); 6.63 (2H, m); 6.94 (2H, d, J=8.7 Hz); 7.25 (1H, m); 7.82 (2H, d; J=8.7)

Melting point=86-90° C.

Example 2

Step b

Preparation of the 3-{4-[2-butyl-5-methanesulfonamide-1-benzofuran-3-yl)carbonyl]phenoxy}propyl methanesulfonate (formula (IV))

124.3 g (1.09 mol) of mesyl chloride in 250 ml of dichloromethane are added dropwise in a solution of 150 g of the compound of step (a) (0.408 mol) and 86.2 g of pyridine (1.09 mol) in 1200 ml of dichloromethane, checking that the temperature does not exceed 10° C. Once the dropwise addition is complete, the reaction mixture is left at room temperature for approximately 24 h. 1000 ml of deionised water, pre-cooled to 0-5° C., are added to the organic phase, and the two phases are mixed for approximately 10 minutes. The aqueous phase is then removed and the dichloromethane is washed in sequence with: 1000 ml of an aqueous solution of HCl 0.1 N, 1000 ml of an aqueous solution of 2% $NaHCO_3$ and 1000 ml of deionised water. The organic phase is dried over $Na_2SO_4$, the salt is filtered and the solvent is evaporated at reduced pressure. 1500 ml of toluene are added to the residue thus obtained, it is heated to reflux until complete dissolution of the solid and left to come back to temperature. It is cooled for 3-4 hours at 0-4° C. and the solid is filtered. The wet product is washed on a filter with approximately 150 ml of toluene pre-cooled to 0-5° C., discharged and dried at 40° C. for 6-7 hours. 197 g of the product of the title are obtained.

Yield 92%

$^1$HNMR ($CDCl_3$, 300 MHz): δ=0.90 (3H, t); 1.35 (2H, m); 1.75 (2H, m); 2.27 (2H, m); 2.90 (3H,s); 2.92 (2H, t); 3.03 (3H, s); 4.21 (2H, t); 4.47 (2H, t); 6.59 (1H, s); 6.96 (2H, d, J=8.7 Hz); 7.10 (1H, d, J=2.2 Hz); 7.26 (1H, dd, J=8.7 Hz, J=2.2 Hz); 7.45 (1H, d, J=8.7); 7.79 (2H, d, J=8.7 Hz).

Melting point=132-136° C.

Example 3

Steps c and d

Preparation of the Dronedarone*HCl) (formula (I)*HCl)

207 g (1.60 mol) of dibutyl amine are added to a suspension of 195 g (0.372 mol) of dimesyl in 1560 ml of acetonitrile. The solution is heated to reflux for 4-5 h. Once the reaction is complete, the mixture is brought to 40-45° C. and the solvent is distilled at reduced pressure. 957 ml of toluene and 750 ml of deionised water are added to the residue. Once the aqueous phase is separated, 750 ml of deionised water are loaded and the pH of the solution is brought to 4.6-4.8 with a solution of 80% acetic acid. It is left under stirring for approximately 5-10 minutes, then the aqueous phase is separated and any interphase formed with the organic phase is maintained. The toluene is washed twice with 750 ml of a 1% solution of NaCl and with 750 ml of a 2% aqueous solution of bicarbonate. The pH of the aqueous phase is checked: if it is around 6.5-7 the water is separated; if it is lower, solid sodium bicarbonate is added until the above value is reached. A further two washing operations of the organic phase are performed with 750 ml of deionised water. 7 g of carbon are added and the toluene phase is left under stirring at 40-50° C. for approximately 1 hour. The solution is hot filtered on a Celite panel and the organic phase without the carbon is concentrated at reduced pressure. The residue thus obtained is dissolved in 585 ml of acetone at 30-35° C. 36.4 g of 37% HCl are added dropwise at this temperature, maintaining the mixture below 40° C. The reaction is left to slowly come back to temperature and after approximately 2 hours it is cooled to 0-5° C. After 1 hour the solid is filtered and the wet product is washed with approximately 150 ml of acetone. The crude dronedarone hydrochloride is re-crystallised from acetone and dried under a vacuum at 40° C. for 6-7 hours. 156 g of dronedarone hydrochloride are obtained.

Yield: 71%

Purity HPLC>99%

$^1$HNMR ($CDCl_3$, 300 MHz): δ=0.90 (3H, t); 0.97 (6H, t); 1.38 (6H, m); 1.61 (1H, s); 1.76 (6H, m); 2.40 (2H, m); 2.90 (3H, s); 2.95 (2H, t); 3.06 (4H, m); 3.24 (2H, m); 4.23 (2H, t); 6.92 (2H, d, J=8.7 Hz,); 7.19 (1H, d, J=2.1); 7.31 (1H, dd, J=8.7, J=2.1); 7.40 (1H, d, J=8.7); 7.76 (2H, d, J=8.7); 11.90 (1H, s).

Melting point=141-145° C.

Example 4

Preparation of the 3-{4-[(2-butyl-5-nitro-1-benzofuran-3-yl)carbonyl]phenoxy}propan-1-ol (formula (II))

312 g (2.26 moles) of potassium carbonate, 11 g (0.066 moles) of potassium iodide and 11 g (0.034 moles) of tetrabutylammonium bromide are added to a solution of 222 g (0.655 moles) of 2-butyl-3-(4-hydroxybenzoyl)-5-nitro-benzofuran (formula (V)) in 1780 ml of DMF. The reaction mixture is heated to 50° C. and after approximately 30 minutes 100 g of 3-chloro-1-propanol are added dropwise. At the end of the dropwise addition, the reaction mixture is brought to 80-85° C. and left under stirring for 4-5 hours. Once the reaction is complete, the mixture is cooled to 40-50° C. and the inorganic salts are removed by filtering. The organic solvent is distilled at reduced pressure, maintaining the temperature around 60-70° C., and the residue is dissolved in 2220 ml of toluene.

After performing three washing operations on the organic phase, each with 1130 ml of deionised water, the toluene is concentrated to residue. The crude product is dissolved with approximately 100 ml of ethyl acetate and the mixture is left under cooling at 0-4° C. for approximately 12 hours. The solid is filtered, the wet product is washed with a little ethyl acetate pre-cooled to 0-5° C. and it is dried under a vacuum at 40° C. for 6-7 hours. 181 g of 3-{4-[(2-butyl-5-nitro-1-benzofuran-3-yl)carbonyl]phenoxyl}propan-1-ol (formula (II)) are obtained.

Yield: 69%

$^1$HNMR (CDCl$_3$, 300 MHz): δ=0.89 (3H, t); 1.37 (2H, m); 1.60 (1H, s); 1.74 (2H, m); 2.08 (2H, m); 2.92 (2H, t); 3.89 (2H, t); 4.23 (2H, t); 6.99 (2H, d, J=8.7 Hz); 7.56 (1H, d, J=9 Hz); 7.82 (2H, d, J=8.7); 8.20 (1H, dd, J=9, J=2.3); 8.32 (1H, d, J=2.3).

Melting point=76-80° C.

The invention claimed is:

1. Process for the preparation of dronedarone of formula (I), or of a salt thereof, which comprises:

(a) reducing the nitro group of the compound of formula (II)

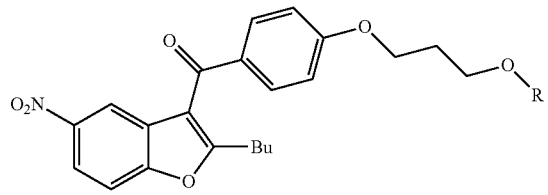

wherein "Bu" represents n-butyl and R represents a protecting group which is cleavable by hydrogenation, to yield the compound of formula (III)

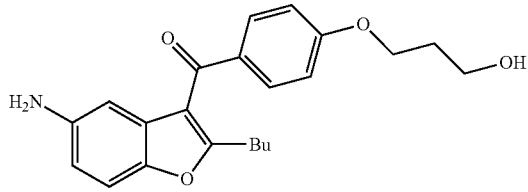

(b) bis-mesylating the compound (III) thus obtained, to yield the compound of formula (IV)

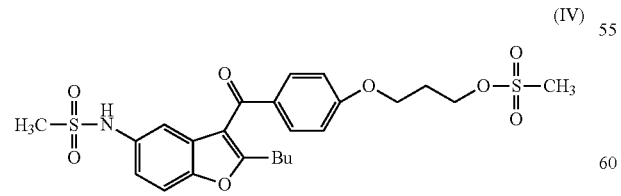

(c) replacing the mesyloxy group of the compound (IV) with a dibutylamino group to obtain dronedarone of formula (I)

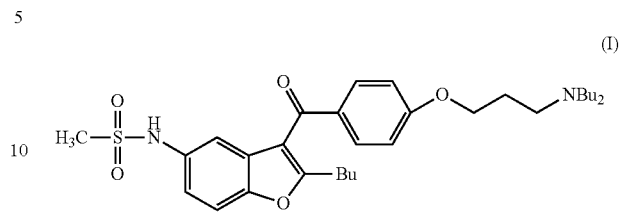

(d) optionally converting dronedarone into a salt thereof.

2. Process according to claim 1, wherein in step (d) dronedarone is converted into its hydrochloride salt.

3. Process according to claim 1, wherein the reduction step (a) is a catalytic reduction.

4. Process according to claim 1, wherein mesylation step (b) is carried out with a mesyl halide.

5. Process according to claim 4, wherein said mesyl halide is mesyl chloride.

6. Process according to claim 1, wherein in the mesylation of step (b), mesyl halide is added at a temperature of 0-5° C.

7. Process according to claim 6, wherein the mesylation of step (b) is then carried out at room temperature.

8. Process according to claim 4, wherein said mesyl halide is used in an at least double the molar amount with respect of the compound of formula (III).

9. Compound of formula (IV)

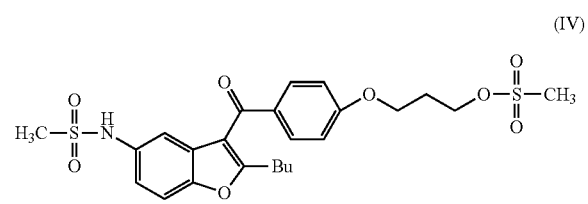

wherein "Bu" represents n-butyl, salts and solvates thereof.

10. Process according to claim 1, wherein the compound of formula (II) is prepared starting from the compound of formula (V)

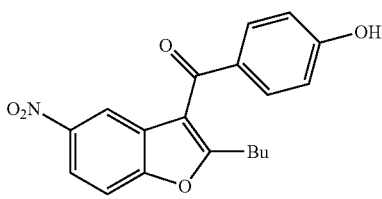

wherein "Bu" represents n-butyl, by reaction with a 3-halo-1-propanol or a protected 3-halo-1-propanol.

* * * * *